United States Patent
Tsuchiya et al.

(10) Patent No.: US 9,970,922 B2
(45) Date of Patent: May 15, 2018

(54) OBSERVATION APPARATUS

(71) Applicant: OLYMPUS CORPORATION, Shibuya-ku, Tokyo (JP)

(72) Inventors: Atsuhiro Tsuchiya, Hachioji (JP); Hiroyuki Okahira, Hachioji (JP); Koichiro Izumi, Fuchu (JP)

(73) Assignee: OLYMPUS CORPORATION, Tokyo (JP)

( * ) Notice: Subject to any disclaimer, the term of this patent is extended or adjusted under 35 U.S.C. 154(b) by 36 days.

(21) Appl. No.: 14/924,234

(22) Filed: Oct. 27, 2015

(65) Prior Publication Data
US 2016/0123868 A1 May 5, 2016

(30) Foreign Application Priority Data
Nov. 4, 2014 (JP) ................................ 2014-224051

(51) Int. Cl.
*G01N 33/483* (2006.01)
*G01J 1/02* (2006.01)
*G01J 1/04* (2006.01)

(52) U.S. Cl.
CPC ........ *G01N 33/4833* (2013.01); *G01J 1/0271* (2013.01); *G01J 1/044* (2013.01)

(58) Field of Classification Search
CPC ..... G01J 1/0271; G01J 1/044; G01N 33/4833
See application file for complete search history.

(56) References Cited

U.S. PATENT DOCUMENTS 3,641,898 A * 2/1972 Kawahara ................ A61B 1/04
396/159
8,017,903 B2 9/2011 Natori et al.
(Continued)

FOREIGN PATENT DOCUMENTS

| JP | 08069772 A | 3/1996 |
| JP | 2009116031 A | 5/2009 |

(Continued)

OTHER PUBLICATIONS

Japanese Office Action dated Feb. 27, 2018 issued in counterpart Japanese Application No. 2014-224051.

*Primary Examiner* — Nathan A Bowers
*Assistant Examiner* — Lydia Edwards
(74) *Attorney, Agent, or Firm* — Holtz, Holtz & Volek PC

(57) ABSTRACT

With the object of preventing deterioration of or damage to a photodetector caused by excessive light by more reliably preventing the excessive light from entering the photodetector, a microscope of the present invention is provided with a high-sensitivity detector, such as an HPD, a GaAsP, an EM-CCD or the like, that detects observation light coming from a specimen, a box-shaped casing that has an opening that allows contained items to be placed therein and removed therefrom and that covers the high-sensitivity detector, a door that can close off the opening of the casing, a switch that restricts light detection by the high-sensitivity detector by turning on and off a drive voltage to be applied to the high-sensitivity detector, and an opening restricting mechanism that allows the opening of the casing in the closed state imposed by the door to be opened only when the light detection by the high-sensitivity detector is restricted by the switch.

14 Claims, 4 Drawing Sheets

(56) References Cited

U.S. PATENT DOCUMENTS

2009/0140129 A1* 6/2009 Natori .................... G02B 21/24
                                                              250/216
2014/0296089 A1* 10/2014 Holmes ................ G01N 35/026
                                                                506/9

FOREIGN PATENT DOCUMENTS

| JP | 2009139475 A | 6/2009 |
|----|--------------|--------|
| JP | 2013076723 A | 4/2013 |

* cited by examiner

OBSERVATION APPARATUS

CROSS-REFERENCE TO RELATED APPLICATIONS

This application is based on Japanese Patent Application No. 2014-224051, the contents of which are incorporated herein by reference.

TECHNICAL FIELD

The present invention relates to an observation apparatus.

BACKGROUND ART

In the related art, there are known observation apparatuses that are provided with a high-sensitivity photodetector, such as a photomultiplier tube (hereinafter, referred to simply as a "PMT") or an EM-CCD, and that prevent deterioration of or damage to the photodetector caused by the entry of excessive light thereto (for example, see Patent Literatures 1 and 2).

With a microscope described in Patent Literature 1, it is judged whether or not light intensity signals exceeding a predetermined threshold have been output from a photodetector over a plurality of continuous pixels, and the HV (High Voltage) to be applied to the photodetector is set to zero if it is judged that there has been such an output. In addition, with an observation apparatus described in Patent Literature 2, a sensor detects the open state of a lid of a black box that accommodates a detector or the like, and the entry of light to the photodetector is blocked by a shutter if it is detected that the lid is in the open state.

CITATION LIST

Patent Literature

{PTL 1} Japanese Unexamined Patent Application, Publication No. 2013-76723
{PTL 2} Japanese Unexamined Patent Application, Publication No. 2009-139475

SUMMARY OF INVENTION

With the microscope described in Patent Literature 1, because the HV to be applied to the photodetector is controlled based on the light intensity signals that are detected by the photodetector itself, excessive light has already entered the photodetector at the point in time when the HV is set to zero. In addition, with the observation apparatus described in Patent Literature 2, because there is a time lag between the time when the sensor detects opening of the lid of the black box and the time when the shutter is completely closed, excessive light enters the photodetector during the time lag.

The present invention provides an observation apparatus with which it is possible to prevent deterioration of and damage to a photodetector caused by excessive light by more reliably preventing excessive light from entering the photodetector.

An aspect of the present invention is an observation apparatus provided with a photodetector that detects observation light coming from a specimen; a casing that has an opening that allows contained items to be placed therein and removed therefrom, that has a light blocking capability, and that covers the photodetector; a lid portion that can close off the opening of the casing and that has a light blocking capability; a light-detection restricting portion that restricts light detection by the photodetector; and an opening restricting portion that allows the opening in the closed state imposed by the lid portion to be opened only when the light detection is restricted by the light-detection restricting portion.

With this aspect, it is possible to prevent the photodetector from detecting light coming from outside the casing by closing off the opening of the casing with the lid portion. In addition, it is possible to restrict the photodetector from detecting the light coming from outside the casing by means of the light-detection restricting portion, even when the opening of the casing is open.

In this case, in the case in which the light detection by the photodetector is not restricted by the light-detection restricting portion, because the opening restricting portion does not allow the opening of the casing to be opened, it is possible to prevent external intense light from being detected by the photodetector due to careless opening of the opening when exchanging the contained items in the casing or the like.

Therefore, it is possible to prevent deterioration of and damage to the photodetector caused by excessive light by more reliably preventing excessive light from entering the photodetector.

The above-described aspect may be provided with a detection optical system that makes light coming from the specimen enter the photodetector, wherein the casing may have a detection optical system and a detection-system accommodating portion that accommodates the detection optical system, and the opening may be provided in the detection-system accommodating portion.

By employing such a configuration, when exchanging the detection optical system in accordance with light to be detected, the opening of the detection-system accommodating portion is prevented from being carelessly opened, and thus, it is possible to prevent intense light coming from the area surrounding the detection optical system from being detected by the photodetector.

In the above-described aspect, the casing may have a specimen accommodating portion that accommodates the specimen and a detection-system accommodating portion, which accommodates the photodetector, and that is connected to the specimen accommodating portion so as to allow the light coming from the specimen accommodating portion to enter, and the opening may be provided in the specimen accommodating portion.

By employing such a configuration, when exchanging the specimen, the opening of the specimen accommodating portion is prevented from being carelessly opened, and thus, it is possible to prevent intense light coming from the area surrounding the specimen to be detected by the photodetector in the detection-system accommodating portion.

In the above-described aspect, the light-detection restricting portion may be formed of a shutter that can block the light coming into the photodetector and a switching portion that switches between blockage and passage of the light by the shutter.

By employing such a configuration, with the switching portion, the photodetector detects the light if the shutter allows the light to pass therethrough, and the light detection by the photodetector is prevented if the shutter blocks the light. Therefore, it is possible to avoid light detection by the photodetector by using a simple configuration.

In the above-described aspect, the light-detection restricting portion may reduce an applied drive voltage that drives the photodetector.

By employing such a configuration, the light detection by the photodetector is suppressed when the application of the drive voltage is reduced. Therefore, it is possible to restrict the light detection by the photodetector with a simple operation. In particular, it is possible to prevent the light detection by the photodetector when application of the drive voltage is stopped.

In the above-described aspect, the light-detection restricting portion may be a switching switch that performs at least one of shutter control, which operates a shutter that can block the light coming into the photodetector, and voltage control, which switches between stopping an applied drive voltage that drives the photodetector and reducing the applied drive voltage.

By employing such a configuration, in the case in which the shutter control is performed by the switching switch, the light detection by the photodetector is restricted by blocking the light with the shutter, and, in addition, in the case in which the voltage control is performed by the switching switch, the light detection by the photodetector is prevented or suppressed. Therefore, in both cases, it is possible to easily and reliably restrict the light detection by the photodetector.

In the above-described aspect, the opening restricting portion may be provided with a locking mechanism that can maintain the lid portion in a state in which the lid portion cannot be opened, and the locking mechanism may be configured so as to work together with the light-detection restricting portion, and switches the lid portion from a state in which the lid portion cannot be opened to a state in which the lid portion can be opened when light detection by the photodetector is restricted by the light-detection restricting portion.

By employing such a configuration, because the locking mechanism maintains the lid portion in the state in which the lid portion cannot be opened when the light detection by the photodetector is not restricted, it is possible to prevent the opening from being carelessly opened in the state in which the photodetector can detect external light.

In the above-described aspect, the light-detection restricting portion may be a switching switch that works together with opening/closing operation of the lid portion, and the opening restricting portion may be a shielding member that, when the lid portion is open, blocks entry of light to the photodetector from the opening until switching to a state in which light detection by the photodetector is restricted is completed by the switching switch that works together with the opening/closing operation.

By employing such a configuration, because the shielding member blocks the entry of light from the opening of the casing until the light detection by the photodetector is restricted, it is possible to prevent the opening from being carelessly opened in the state in which the photodetector can detect external light.

In the above-described aspect, the specimen accommodating portion may have a culturing space in which the specimen such as a living cell can be maintained at a certain temperature.

By employing such a configuration, by using the culturing space, the specimen accommodated in the specimen accommodating portion can be observed in vivo.

The present invention affords an advantage in that it is possible to prevent deterioration of and damage to a photodetector caused by excessive light by more reliably preventing excessive light from entering the photodetector.

DESCRIPTION OF EMBODIMENTS

First Embodiment

A microscope (observation apparatus) according to a first embodiment of the present invention will be described below with reference to the drawings.

Figure 1:
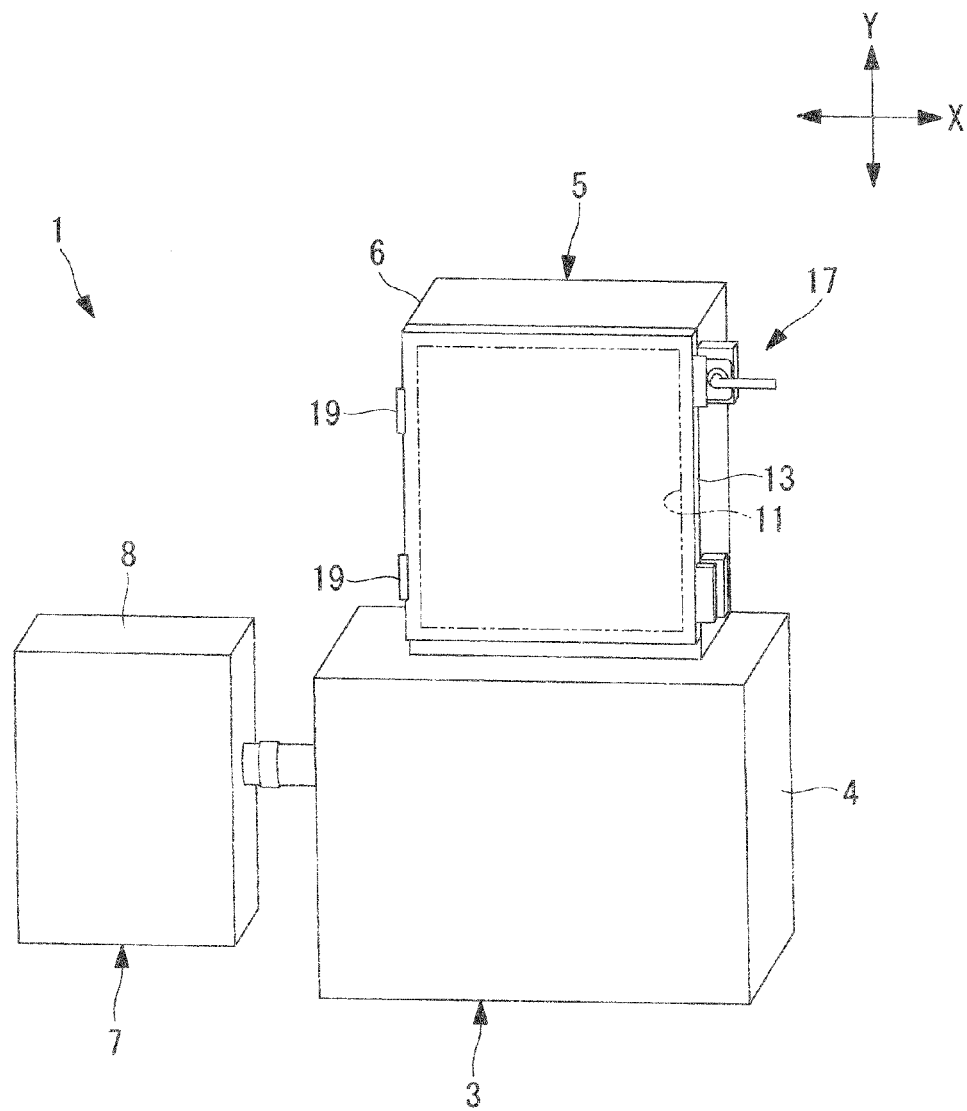
FIG. 1 is a diagram showing, in outline, the configuration of a microscope according to a first embodiment of the present invention.

As shown in FIG. 1, a microscope 1 according to this embodiment is provided with an optical unit 3 that includes, among others, a scanner (not shown) that two dimensionally scans laser light emitted from a light source (not shown), such as a galvanometer mirror, and a dichroic mirror that splits optical paths of the laser light and observation light; a culturing unit 5 that includes, among others, an objective lens (not shown) with which the laser light is radiated onto a specimen (not shown); and a detection unit 7 that includes, among others, a high-sensitivity detector (photodetector, not shown) that detects light coming from the specimen that has been irradiated with the laser light.

The optical unit 3 is provided with a rectangular box-shaped casing 4 that accommodates the scanner, the dichroic mirror, and so forth.

The culturing unit 5 is provided with a cubic box-shaped casing (specimen accommodating portion) 6 that accommodates the specimen, the objective lens, and so forth.

The detection unit 7 is provided with a casing (detection-system accommodating portion) 8 that accommodates the high-sensitivity detector and so forth. Examples of the high sensitivity detector include an HPD (Hybrid Photodetector), a GaAsP (gallium arsenide phosphide)-type PMT (Photomultiplier-tube), an EM-CCD (Electron Multiplying COD), and so forth.

All of these casings 4, 6, and 8 are formed of a light-blocking material and are connected so as to allow the laser light or the observation light to enter thereto and exit therefrom. Specifically, the casing 4 and the casing 6 are connected so that the laser light scanned by the scanner in the optical unit 3 enters the culturing unit 5 and so that, on the other hand, the observation light coming from the specimen in the culturing unit 5 enters the optical unit 3. In addition, the casing 4 and the casing 8 are connected so that the observation light that has been split off by the dichroic mirror in the optical unit 3 enters the detection unit 7. The light source and the casing 4 are also connected.

In the culturing unit 5, in order to observe live specimens such as living cells, the casing 6 thereof forms a culturing space in which a specimen can be maintained at a certain temperature, and the culturing unit 5 is configured so that a culturing vessel (not shown) that accommodates the specimen can be placed in the culturing space. This casing 6 has an opening 11 provided at the front side thereof, which allows the specimen (contained items) or the like to be exchanged. In the following, in FIG. 1 in which the opening 11 of the casing 6 is viewed from the front, the width direction of the casing 6 is assumed to be the X-direction, and the height direction of the casing 6 is assumed to be the Y-direction.

Figure 2:
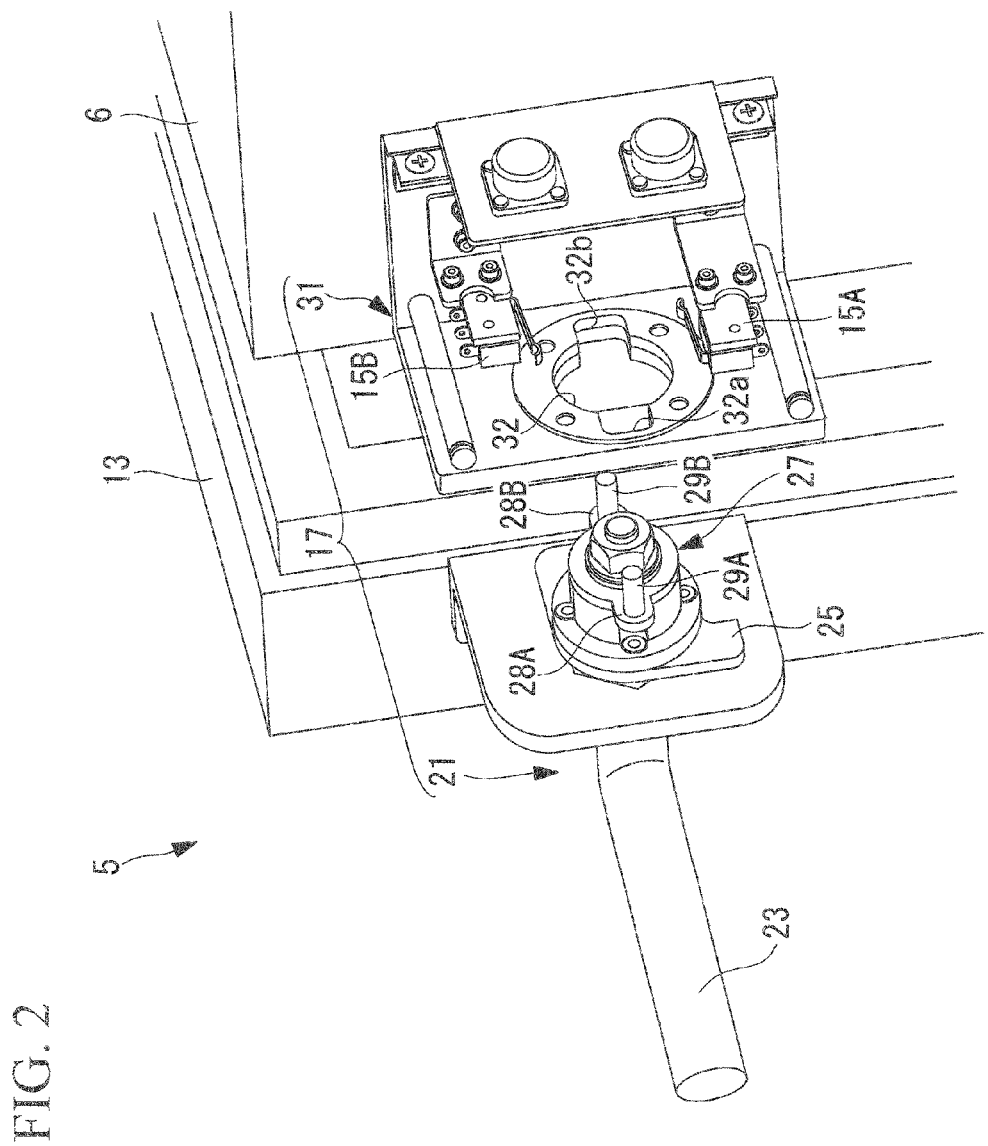
FIG. 2 is a diagram showing a state in which an opening of a casing of a culturing unit in the microscope in FIG. 1 is open.
Figure 3:
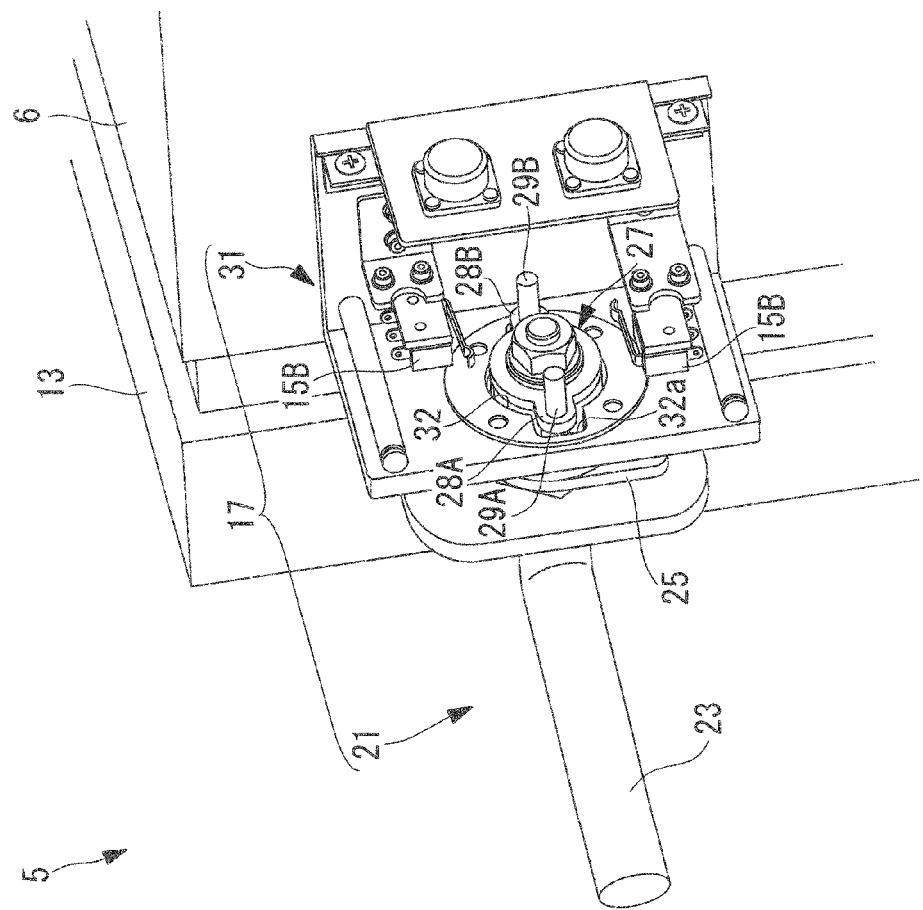
FIG. 3 is a diagram showing a state in which the opening of the casing in FIG. 2 can be opened.

In addition, as shown in FIGS. 2 and 3, the culturing unit 5 is provided with a door (lid portion) 13 that can close off the opening 11 of the casing 6, two switches (Light-detection restricting portions, switching switches) 15A and 15B for turning on and off the drive voltage to be applied to the high sensitivity detector in the detection unit 7, and an opening restricting mechanism (opening restricting portion) 17 that prevents the door 13 from opening the opening 11.

The door 13 is formed in a substantially flat plate shape by using a light-blocking material. As shown in FIG. 1, this door 13 is attached to the opening 11 by means of hinges 19 that are secured to the casing 6 at one side thereof near the opening 11 so as to allow the opening 11 to be opened and closed.

As shown in FIGS. 2 and 3, the opening restricting mechanism 17 is constituted of a door-side locking mechanism (locking mechanism) 21 attached to the side surface opposite from the hinges 19 of the door 13 and a casing-side locking mechanism (locking mechanism) 31 that is attached to the casing 6 near the opening 11 at the side surface opposite from the hinges 19 and that is capable of immobilizing the door-side locking mechanism 21 in the state in which the door 13 is closed.

The door-side locking mechanism 21 is constituted of a handle 23 that is a bar bent at substantially a right angle so as to be shaped like the letter L, a support portion 25 that is secured to a side surface of the door 13 and that supports the handle 23, and a ring-shaped fitting portion 27 that is fitted to the tip of a shorter arm of the handle 23.

The handle 23 is supported by the support portion 25 with the tip of the shorter arm thereof pointing toward the casing 6 so that a user can hold a longer arm thereof.

The support portion 25 supports the shorter arm of the handle 23 so as to be rotatable about a shaft extending in the plate-thickness direction of the door 13.

The ring-shaped fitting portion 27 is formed in a substantially ring shape and has two flanges 28A and 28B that extend radially outward in opposite directions from each other. Two push pins 29A and 29B that protrude in directions parallel to the center axial direction of the ring-shaped fitting portion 27 are attached to the flanges 28A and 28B.

The ring-shaped fitting portion 27 is secured to the shorter arm of the handle 23 such that the ring-shaped fitting portion 27 is positioned about the center axis so that the push pins 29A and 29B point in the direction in which the tip of the shorter arm of the handle 23 faces and so that the direction in which the flanges 28A and 28B are arrayed is aligned with the direction parallel to the longer arm of the handle 23.

The casing-side locking mechanism 31 has a through-hole 32 into which the ring-shaped fitting portion 27 of the door-side locking mechanism 21 can be inserted. The through-hole 32 is formed in a slightly larger size than the ring-shaped fitting portion 27 and has two notches 32a and 32b that extend radially outward so as to correspond with the shapes of the flanges 28A and 28B. The notches 32a and 32b are formed side-by-side in the X-direction.

The thus-configured opening restricting mechanism 17 is formed so that the ring-shaped fitting portion 27 of the door-side locking mechanism 21 can be made to pass through the through-hole 32 of the casing-side locking mechanism 31 when the flanges 28A and 28B of the ring-shaped fitting portion 27 of the door-side locking mechanism 21 and the notches 32a and 32b of the through-hole 32 of the casing-side locking mechanism 31 are aligned with each other in terms of their positions about the shaft. By making the ring-shaped fitting portion 27 of the door-side locking mechanism 21 pass through the through-hole 32 of the casing-side locking mechanism 31, it is possible to open the opening 11 by opening the door 13, as shown in FIG. 2, and to completely close off the opening 11 by closing the door 13, as shown in FIG. 3.

In addition, when the handle 23 is rotated about the shaft in the state in which the ring-shaped fitting portion 27 is inserted into the through-hole 32 so as to shift the flanges 28A and 28B of the ring-shaped fitting portion 27 and the notches 32a and 32b of the through-hole 32 in terms of their positions about the shaft, the flanges 28A and 28B are stopped by the through-hole 32, thus preventing the door 13 from being opened, which also prevents the opening 11 of the casing 6 from being opened. The state in which the flanges 28A and 28B of the ring-shaped fitting portion 27 inserted into the through-hole 32 are shifted about the shaft by 90° with respect to the notches 32a and 32b of the through-hole 32 will be referred to as a locked state.

The switches 15A and 15B restrict the light detection by the high-sensitivity detector by turning on and off the drive voltage to be applied to the high-sensitivity detector in the detection unit 7. These switches 15A and 15B are mounted in the vicinity of the through-hole 32 of the casing-side locking mechanism 31 so that the push pins 29A and 29B come into contact with the switches 15A and 15B, respectively, when the door-side locking mechanism 21 is in the locked state.

In addition, when the switches 15A and 15B are pressed by coming into contact with the push pins 29A and 29B, the drive voltage for the high sensitivity detector is turned on, and, when the push pins 29A and 29B are moved away from the switches 15A and 15B, thus releasing the pressing thereof, the drive voltage for the high sensitivity detector is turned off.

Therefore, the opening restricting mechanism 17 allows the opening 11 in the closed state imposed by the door 13 to be opened only when the drive voltage is turned off by the switches 15A and 15B.

The operation of the thus-configured microscope 1 will now be described.

In order to observe a specimen by using the microscope 1 according to this embodiment, the user opens the door 13 of the casing 6 in the culturing unit 5, and places the culturing vessel accommodating the specimen in the culturing unit 5.

Next, as shown in FIG. 2, the user holds the handle 23 and aligns the flanges 28A and 28B of the ring-shaped fitting portion 27 of the door-side locking mechanism 21 and the notches 32a and 32b of the through-hole 32 of the casing-side locking mechanism 31 in terms of their positions about the shaft, inserts the ring-shaped fitting portion 27 into the through-hole 32, as shown in FIG. 3, and closes the door 13. By doing so, the opening 11 of the casing 6 is closed off by the door 13.

Subsequently, by rotating the handle 23 about the shaft in the state in which the ring-shaped fitting portion 27 is inserted into the through-hole 32, the flanges 28A and 28B of the ring-shaped fitting portion 27 and the notches 32a and 32b of the through-hole 32 are shifted about the shaft by 90°. By doing so, the push pins 29A and 29B of the ring-shaped fitting portion 27 press the switches 15A and 15B, respectively, and thus, the switches 15A and 15B turn on the drive voltage for the high-sensitivity detector.

Next, the laser light is emitted from the light source. The laser light emitted from the light source is two-dimensionally scanned by the scanner and is radiated onto the specimen by means of the objective lens. The observation light generated at the specimen by being irradiated with the laser light is collected by the objective lens, travels back along the optical path of the laser light, is split off from this optical path by the dichroic mirror, and is detected by the high-sensitivity detector. For example, it is possible to generate image information of the specimen based on the intensity signals output from the high-sensitivity detector by using a PC (Personal Computer: not shown).

Next, the procedures for exchanging the specimen with another one will be described.

To exchange the specimen with another one in the microscope 1 according to this embodiment, the user holds the handle 23 and rotates the ring-shaped fitting portion 27 in the locked state about the shaft. Once the ring-shaped fitting portion 27 begins to rotate, the push pins 29A and 29B are moved away from the switches 15A and 15B, which releases the pressing on the switches 15A and 15B by the push pins 29A and 29B, and thus, the drive voltage for the high-sensitivity detector is turned off by the switches 15A and 15B.

Then, as shown in FIG. 3, the ring-shaped fitting portion 27 is released from the through-hole 32 when the flanges 28A and 28B of the ring-shaped fitting portion 27 and the notches 32a and 32b of the through-hole 32 are aligned with each other in terms of their positions about the shaft. By doing so, as shown in FIG. 2, the door 13 is opened, thus opening the opening 11 of the casing 6. Therefore, it is possible to exchange the specimen in the casing 6 with another one.

As has been described above, with the microscope 1 according to this embodiment, because the opening restricting mechanism 17 does not allow the opening 11 of the casing 6 to be opened when the drive voltage to be applied to the high-sensitivity detector is not turned off by the switches 15A and 15B, it is possible to prevent external intense light from being detected by the high-sensitivity detector due to careless opening of the opening 11 when exchanging the contained item such as the specimen with another one or the like.

In addition, because there is a time lag between the time at which the drive voltage is turned off by the switches 15A and 15B after the ring-shaped fitting portion 27 begins to rotate from the locked state, in which the flanges 28A and 28B of the ring-shaped fitting portion 27 of the door-side locking mechanism 21 and the notches 32a and 32b of the through-hole 32 of the casing-side locking mechanism 31 are shifted by 90° in terms of their positions about the shaft, and the time at which the flanges 28A and 28B of the ring-shaped fitting portion 27 and the notches 32a and 32b of the through-hole 32 are aligned with each other in terms of their positions about the shaft, it is possible to reliably turn off the voltage to be applied to the high-sensitivity detector before the state in which the door 13 can be opened is achieved.

Therefore, it is possible to prevent deterioration and or damage to the high-sensitivity detector caused by excessive light by more reliably preventing the excessive light from entering the high-sensitivity detector.

Second Embodiment

Next, a microscope (observation apparatus) according to a second embodiment of the present invention will be described.

Figure 4:
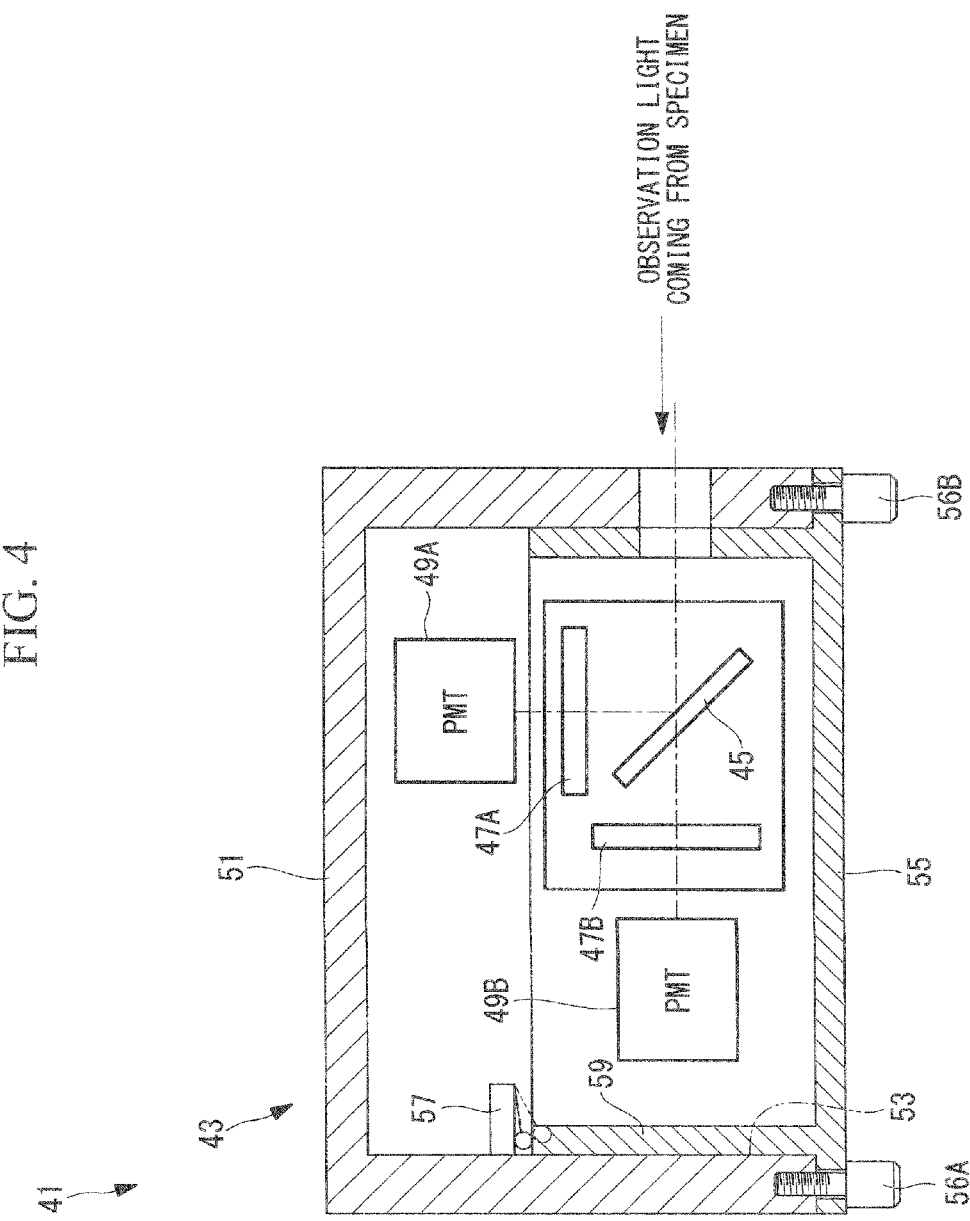
FIG. 4 is a diagram showing, in outline, the configuration of a detection unit of a microscope according to a second embodiment of the present invention.

As shown in FIG. 4, a microscope 41 according to this embodiment differs from that of the first embodiment in that a detection unit 43 that includes a casing 51 having an opening 53 is provided instead of the detection unit 7.

In the following, configurations shared with the microscope 1 according to the first embodiment will be given the same reference signs, and descriptions thereof will be omitted. In addition, because the optical unit 3 and the culturing unit 5 are the same as those of the first embodiment, descriptions thereof will be omitted.

The detection unit 43 is provided with a spectral dichroic mirror (detection optical system) 45 that splits the optical path of the observation light that enters from the optical unit 3 by reflecting or transmitting the light depending on the wavelengths thereof, a barrier filter (detection optical system) 47A that blocks laser light included in the observation light that has been reflected by the spectral dichroic mirror 45 and that travels along one of the optical paths, a PMT 49A that detects the observation light that has passed through the barrier filter 47A, a barrier filter (detection optical system) 47B that blocks laser light included in the observation light that has been transmitted by the spectral dichroic mirror 45 and that travels along the other optical path, and a PMT 49B that detects the observation light that has passed through the barrier filter 47B.

In addition, the detection unit 43 is provided with a casing (detection-system accommodating portion) 51 that accommodates the above-described spectral dichroic mirror 45, barrier filters 47A and 47B, PMTs (Photomultiplier Tubes, photodetectors) 49A and 49B, and so forth, a lid (lid portion) 55 that can close off the opening 53 of the casing 51, a switch (light-detection restricting portion, switching switch) 57 that turns on and off the drive voltage to be applied to the PMTs 49A and 49B, and a shielding portion (opening restricting portion, shielding member) 59 that is integrally formed with the lid 55 and that can be fitted to the opening 53 of the casing 51.

The casing 51 is connected to the casing of the optical unit 3 so that the observation light that has been split off by the dichroic mirror in the optical unit 3 enters the detection unit 43. In addition, the casing 51 is formed in a cubic box shape by using a material having light blocking capability, and has the opening 53 provided at the front side thereof, which allows the spectral dichroic mirror 45 and/or the barrier filters 47A and 47B to be exchanged with another one(s).

The lid 55 is formed in a flat plate shape by using a material having light blocking capability so as to have a large enough size to close off the opening 53 of the casing 51. This lid 55 has two securing knobs 56A and 56B that pass therethrough in the plate-thickness direction. The securing knobs 56A and 56B are disposed at positions that correspond to circumferential edge portions of the opening 53 in the casing 51.

In addition, the securing knobs 56A and 56B are configured so that the lid 55 that closes off the opening 53 can be secured to the casing 51 when the user holds first ends of the securing knobs 56A and 56B that protrude to the front side of the lid 55, inserts the second ends thereof that protrude to the back side of the lid 55 into the circumferential edge portions of the opening 53 of the casing 51, and fastens the securing knobs 56A and 56B thereto.

The shielding portion 59 is formed in a rectangular frame shape that can shield the opening 53 of the casing 51 over the circumference thereof by using the light-blocking material, as with the lid 55. In addition, the shielding portion 59 protrudes from the back side of the lid 55 in the plate-thickness direction, and has a long enough length to deeply reach into the interior of the casing 51 in the state in which the lid 55 is secured to the casing 51.

The switch 57 is secured to an inner wall surface of the casing 51. This switch 57 is configured so as to turn on the drive voltages for the PMTs 49A and 49B by being pressed by the distal end of the shielding portion 59 when the lid 55 closes off the opening 53 of the casing 51. In addition, the switch 57 is configured so as to turn off the drive voltages for the PMTs 49A and 49B when the shielding portion 59 of the lid 55 is moved away, thus releasing the pressing on the switch 57.

The operation of the thus-configured microscope 41 will now be described.

In order to observe a specimen by using the microscope 41 according to this embodiment, as with the first embodiment, the laser light is radiated onto the specimen, and the observation light coming from the specimen is made to enter the detection unit 43 via the optical unit 3.

At the detection unit 43, the observation light from the optical unit 3 is split off by the spectral dichroic mirror 45 in accordance with the wavelengths thereof. The observation light that has been reflected by the spectral dichroic mirror 45 passes through the barrier filter 47A and is detected by the PMT 49A, and the observation light that has been transmitted by the spectral dichroic mirror 45 passes through the barrier filter 47B and is detected by the PMT 49B. It is possible to generate image information of the specimen based on the intensity signals output from the PMTs 49A and 49B by means of the PC.

Next, the procedures for exchanging the spectral dichroic mirror 45 and/or the barrier filters 47A and 47B with another one(s) will be described.

To exchange the spectral dichroic mirror 45 and/or the barrier filters 47A and 47B with another one(s) in the microscope 41 according to this embodiment, the user holds the securing knobs 56A and 56B of the lid 55 of the detection unit 43 and removes the lid 55 from the opening 53 of the casing 51. The drive voltages are turned off by the switch 57 when the distal end of the shielding portion 59 is moved away from the switch 57, thus releasing the pressing on the switch 57.

Because the shielding portion 59 shields the circumference of the opening 53 of the casing 51 and is also inserted deep into the interior thereof, there is a time lag between the time at which the drive voltages are turned off after the lid 55 is started to be removed and the distal end of the shielding portion 59 is moved away from the switch 57 and the time at which the shielding portion 59 is completely removed from the opening 53. Therefore, it is possible to exchange the spectral dichroic mirror 45 and/or the barrier filters 47A and 47B with another one(s) by opening the opening 53 only in the state in which the light detection by the PMTs 49A and 49B is reliably turned off.

In FIG. 4, a hole through which the observation light coming from the specimen passes is provided in the casing 51, and, although a similar hole is also provided in the shielding portion 59, the switch 57 is configured so as to be turned off before the hole in the shielding portion 59 is exposed outside the casing 51 after starting to remove the lid 55.

Once exchanging of the spectral dichroic mirror 45 and/or the barrier filters 47A and 47B with another one(s) is completed, the lid 55 is closed by fitting the shielding portion 59 of the lid 55 to the opening 53 of the casing 51, and the lid 55 is secured to the casing 51 by means of the securing knobs 56A and 56B. Once the opening 53 is completely closed off by the lid 55, the distal end of the shielding portion 59 presses the switch 57, which makes the switch 57 turn on the drive voltages for the PMTs 49A and 49B.

As has been described above, with the microscope 41 according to this embodiment, because the shielding portion 59 does not allow the opening 53 of the casing 51 to be opened when the drive voltages to be applied to the PMTs 49A and 49B are not turned off by the switch 57, it is possible to prevent external intense light from being detected by the PMTs 49A and 49B due to careless opening of the opening 53 when exchanging the spectral dichroic mirror 45 and/or the barrier filters 47A and 47B with another one(s) or the like.

Therefore, it is possible to prevent deterioration of and damage to the PMTs 49A and 49B caused by excessive light by more reliably preventing the excessive light from entering the PMTs 49A and 49B.

Although this embodiment has been described assuming that, as with the first embodiment, the specimen is accommodated in the culturing unit 5, this embodiment is applicable even in a state in which the specimen is not accommodated in the culturing unit 5 and the area surrounding the specimen is not shielded from light. In this case, although external light coming from the area surrounding the specimen may potentially enter the PMTs 49A and 49B, the influence of the external light coming from the area surrounding the specimen can be reduced by using the microscope 41 in a darkroom. However, when the lid 55 is opened when exchanging the spectral dichroic mirror 45 and/or the barrier filters 47A and 47B or the like with another one(s), the PMTs 49A and 49B may be deteriorated even in a darkroom depending on the light level of a liquid crystal display or the like. With the microscope 41 according to this embodiment, it is possible to effectively protect the PMTs 49A and 49B even in such a case.

In the individual embodiments described above, although the switches 15A, 15B, and 57 turn off the drive voltages for the high sensitivity detector and the PMTs 49A and 49B, it suffices to prevent deterioration of the high sensitivity detector and the PMTs 49A and 49B by suppressing detection of excessive light by the high-sensitivity detector and the PMTs 49A and 49B by reducing the drive voltages therefor. For example, it is permissible that the switches 15A, 15B, and 57 do not turn off the drive voltages but reduce them as much as possible.

In addition, in the individual embodiments described above, although the switches 15A, 15B, and 57 that turn off the drive voltages to be applied to the high-sensitivity detector and the PMTs 49A and 49B have been described as examples of the light-detection restricting portion, alternatively, for example, a shutter that can block light coming into the PMTs 49A and 49B and a switch that switches between blockage and passage of light by the shutter may be employed as light-detection restricting portions.

In this case, for example, a shutter that can be opened and closed in the optical path of light coming into the high-sensitivity detector and the PMTs 49A and 49B and a switch that switches between passage and blockage of the light by opening and closing the shutter may be employed, or a shutter than can be inserted into and removed from the optical path of light coming into the PMTs 49A and 49B and a switch that switches between blockage and passage of the light by inserting/removing the shutter into/from the optical path may be employed.

As above, although the embodiments of the present invention have been described in detail with reference to the drawings, specific configurations thereof are not limited to those of the embodiments, and design alterations or the like within a range that does not depart from the scope of the present invention are also encompassed. For example, the present invention is not limited to forms applied to the individual embodiments described above and modifications thereof, the present invention may be applied to embodiments in which these embodiments and modifications are appropriately combined, and it is not particularly limited.

REFERENCE SIGNS LIST 1, 41 microscope
4 casing
6 casing (casing, specimen accommodating portion)
8 casing (casing, detection-system accommodating portion)
13 door (lid portion)
15A, 15B switch (light-detection restricting portion, switching switch)
17 opening restricting mechanism (opening restricting portion)
21 door-side locking mechanism (locking mechanism)
31 casing-side locking mechanism (locking mechanism)
45 spectral dichroic mirror (detection optical system)
47A, 47B barrier filter (detection optical system)
49A, 49B PMT (photodetector)
51 casing (casing, detection-system accommodating portion)
55 lid (lid portion)
57 switch (light-detection restricting portion, switching switch)
59 shielding portion (opening restricting portion, shielding member)

The invention claimed is:

1. An observation apparatus comprising:
a photodetector that detects observation light coming from a specimen;
a casing that has an opening that allows contained items to be placed therein and removed therefrom, that has a light blocking capability, and that covers the photodetector;
a lid that can close off the opening of the casing and that has a light blocking capability;
a locking mechanism configured to lock the lid in a state in which the lid cannot be opened, wherein the locking mechanism is movable between a locked state in which the lid is locked, and an unlocked state in which the lid is openable; and
light-detection restricting means for restricting light detection by the photodetector while the locking mechanism moves from the locked state to the unlocked state and before the locking mechanism reaches the unlocked state in which the lid is openable, and for not restricting light detection by the photodetector when the locking mechanism is in the locked state.

2. The observation apparatus according to claim 1, wherein the light-detection restricting means comprises a switch that switches between (i) a state in which a drive voltage that drives the photodetector is applied, and (ii) a state in which the applied drive voltage is stopped or reduced;
wherein the locking mechanism cooperates with the switch such that the switch is turned on to apply the drive voltage that drives the photodetector when the locking mechanism is in the locked state, and such that the switch is turned off to stop or reduce the applied drive voltage while the locking mechanism moves from the locked state to the unlocked state and before the locking mechanism reaches the unlocked state in which the lid is openable.

3. The observation apparatus according to claim 2, wherein the locking mechanism comprises a pin which engages the switch such that the switch is turned on to apply the drive voltage that drives the photodetector when the locking mechanism is in the locked state, and which is disengaged from the switch such that the switch is turned off to stop or reduce the applied drive voltage while the locking mechanism moves from the locked state to the unlocked state and before the locking mechanism reaches the unlocked state in which the lid is openable.

4. The observation apparatus according to claim 1, wherein the light-detection restricting means comprises:
a shutter configured to block and unblock an optical path of light to the photodetector; and
a switch configured to switch the shutter between blocking and unblocking the optical path.

5. The observation apparatus according to claim 1, further comprising:
a detection optical system that makes light coming from the specimen enter the photodetector,
wherein the casing includes a detection-system accommodating portion that accommodates the detection optical system, and the opening is provided in the detection-system accommodating portion.

6. The observation apparatus according to claim 1, wherein the casing includes a specimen accommodating portion that accommodates the specimen and a detection-system accommodating portion, which accommodates the photodetector, and that is connected to the specimen accommodating portion so as to allow the light coming from the specimen accommodating portion to enter, and the opening is provided in the specimen accommodating portion.

7. The observation apparatus according to claim 6, wherein the specimen accommodating portion has a culturing space in which the specimen can be maintained at a certain temperature.

8. An observation apparatus comprising:
a photodetector that detects observation light coming from a specimen;
a casing that has an opening that allows contained items to be placed therein and removed therefrom, that has a light blocking capability, and that covers the photodetector;
a lid that can close off the opening of the casing and that has a light blocking capability, wherein the lid has a shielding portion protruding therefrom that is insertable into the casing, and wherein the lid and the shielding portion are removable from the casing to open the casing; and
light-detection restricting means for restricting light detection by the photodetector while the lid and the shielding portion are being removed from the casing and before the shielding portion is removed from the casing, and for not restricting light detection by the photodetector when the shielding portion is fully inserted into the casing.

9. The observation apparatus according to claim 8, wherein the light-detection restricting means comprises a switch that switches between (i) a state in which a drive voltage that drives the photodetector is applied, and (ii) a state in which the applied drive voltage is stopped or reduced.

10. The observation apparatus according to claim 9, wherein the lid shielding portion engages the switch such that switch is turned on to apply the drive voltage that drives the photodetector when the shielding portion is inserted into the casing, and disengages from the switch such that the switch is turned off to stop or reduce the applied drive voltage while the lid is being removed from the casing and while said shielding portion remains inserted in the casing.

11. The observation apparatus according to claim 8, wherein the light-detection restricting means comprises:
   a shutter configured to block and unblock an optical path of light to the photodetector; and
   a switch configured to switch the shutter between blocking and unblocking the optical path.

12. The observation apparatus according to claim 8, further comprising:
   a detection optical system that makes light coming from the specimen enter the photodetector,
   wherein the casing includes a detection-system accommodating portion that accommodates the detection optical system, and the opening is provided in the detection-system accommodating portion.

13. The observation apparatus according to claim 8, wherein the casing includes a specimen accommodating portion that accommodates the specimen and a detection-system accommodating portion, which accommodates the photodetector, and that is connected to the specimen accommodating portion so as to allow the light coming from the specimen accommodating portion to enter, and the opening is provided in the specimen accommodating portion.

14. The observation apparatus according to claim 13, wherein the specimen accommodating portion has a culturing space in which the specimen can be maintained at a certain temperature.

\* \* \* \* \*